United States Patent
Wong (10) Patent No.: US 7,284,382 B2
(45) Date of Patent: Oct. 23, 2007

(54) APPARATUS AND METHOD FOR CONTROLLING A FAN, COOLING UNIT AND A FRESH AIR DAMPER OF AN AIR CONDITIONER THROUGH USE OF A CAPNO-SWITCH

(76) Inventor: Jacob Y. Wong, 7110 Georgetown Rd., Goleta, CA (US) 93117

( * ) Notice: Subject to any disclaimer, the term of this patent is extended or adjusted under 35 U.S.C. 154(b) by 159 days.

(21) Appl. No.: 10/684,164

(22) Filed: Oct. 10, 2003

(65) Prior Publication Data
US 2005/0076655 A1 Apr. 14, 2005

(51) Int. Cl.
F25D 17/08 (2006.01)
(52) U.S. Cl. .............................. 62/178; 62/78; 165/248
(58) Field of Classification Search .................... 62/78, 62/409–411, 177–178; 165/248–250, 237; 236/49.3
See application file for complete search history.

(56) References Cited

U.S. PATENT DOCUMENTS

| | | | | | |
|---|---|---|---|---|---|
| 4,437,608 | A | * | 3/1984 | Smith | 236/13 |
| 4,505,259 | A | * | 3/1985 | Seppanen et al. | 126/586 |
| 5,340,986 | A | * | 8/1994 | Wong | 250/343 |
| 5,394,934 | A | * | 3/1995 | Rein et al. | 165/200 |
| 5,407,002 | A | * | 4/1995 | Voll | 165/11.1 |
| 6,196,468 | B1 | * | 3/2001 | Young | 236/46 R |
| 6,514,138 | B2 | * | 2/2003 | Estepp | 454/229 |
| 6,578,770 | B1 | * | 6/2003 | Rosen | 236/49.3 |
| 2003/0181158 | A1 | * | 9/2003 | Schell et al. | 454/229 |

* cited by examiner

Primary Examiner—William E. Tapolcai
(74) Attorney, Agent, or Firm—Wagner, Anderson & Bright, LLP; Roy L. Anderson (57) ABSTRACT

A fresh air controller interfaces directly with the electromechanical circuit of an air-conditioner to control its operating settings based upon detected Carbon Dioxide ($CO_2$) level in Parts-Per-Million (PPM) using a "Capno-Switch" which is in essence a specially designed single-beam NDIR $CO_2$ sensor enhanced with features and specifications to render it rugged, compact and very low-cost; unlike conventional single-beam NDIR $CO_2$ sensors, the "Capno-Switch" is capable of providing long-term stability and accuracy in $CO_2$ measurements. The operating settings it can control for the air-conditioner include 1) shutting off the fan, cooling unit and fresh air damper to save energy when the detected $CO_2$ level in the cold air duct is less than 600 PPM; 2) turning on only the fan when the $CO_2$ level is between 600-1,000 PPM; 3) turning on both the fan and the cooling unit when the $CO_2$ level is between 1,000-2,000 PPM and 4) starting to open the fresh air damper to let fresh air in when the $CO_2$ level is in excess of 2,000 PPM. With the incorporation of the "Capno-Switch" as a fresh air controller, air-conditioners can now provide good indoor air quality while at the same time save energy by effectively shutting itself down when nobody is detected to be present.

29 Claims, 4 Drawing Sheets

Functional layout for the "Capno-Switch"

Figure 1. Functional layout for the "Capno-Switch"

Figure 2. Graph showing the electrical power versus incandescent lamp resistance for a constant voltage lamp driver circuit and a quasi-constant power lamp driver circuit Figure 3. Schematic diagram of a typical quasi-constant power driver circuit Figure 4. The P, Q and R branches of the Carbon Dioxide ($CO_2$) infrared absorption band at 4.26 microns or 2,347 cm-1 with absorbance (base 10) versus wavenumber (cm-1)

APPARATUS AND METHOD FOR CONTROLLING A FAN, COOLING UNIT AND A FRESH AIR DAMPER OF AN AIR CONDITIONER THROUGH USE OF A CAPNO-SWITCH

FIELD OF THE INVENTION

The present invention is in the field of appliance controllers and, more specifically, an electronic controller useful in regulating air conditioners having a fan, a cooling unit and a fresh air damper.

BACKGROUND OF THE INVENTION

The importance of ventilation or the bringing in of fresh outside air into one's abode has been recognized since the beginning of civilization. That is the reason why no matter what shapes or forms one's dwelling might take, from the simplest of cabins and huts to the most sophisticated houses and mansions, it always has a number of windows, or one or more doors, whose purpose is to bring in fresh air from the outside in case of need. This simply reflects the fact that as long as people live inside an enclosed space, there will always be a buildup of various forms of airborne dirt or contamination, otherwise generally known as air pollution, that one has to get rid of or neutralize. Ventilation or the bringing in of fresh outdoor air is the most convenient way to remedy the situation as long as there are windows or doors to open. Quoting a century-old French saying, "It is dilution (through adequate ventilation) that is the best solution to pollution!"

Poor indoor air quality within a dwelling has a number of ill and serious ramifications, including fatal accidents. The buildup of poisonous Carbon Monoxide (CO) due to the malfunctioning of gas furnaces or the careless burning of combustibles indoors to get warmth, such as wood, charcoal or liquid fuel, can cost the lives of the inhabitants. An inadequately ventilated indoor space will lead over time, especially when low humidity (<60% Relative Humidity) is not maintained, to indoor air that is full of harmful substances such as mold spores and microbes, dust particles, volatile organic chemicals, airborne germs including viruses and bacteria etc. that will exacerbate the suffering of people with asthma or other respiratory diseases. Indeed, if there is more than one person living in a small enough space that is not properly ventilated, literally speaking, one is breathing other people's air from inside their bodies and vice versa. In other words, if one person has the flu or flu-like illness, the germs that he or she is exhaling into the space will not be able to readily leave the space and the probability of other persons living with him or her getting the same illness will be very much higher. The ill effects of inadequate ventilation can even be felt outside of one's home. The most well-known examples are classrooms at school, insides of school buses or even passenger cabins of airplanes. That is the reason why many people are wary about sending their off-spring to school or themselves traveling by air during the flu season.

In modern day living, with the availability of air-handling appliances such as air-conditioners and heating furnaces, good indoor air quality attained via adequate ventilation is often compromised at the expense of comfort and/or energy or money savings. An important example is the air-conditioner. Most of today's air-conditioners only deal with bringing fresh outdoor air into the conditioned space via a manually adjustable fresh air damper. Since there is no easy way today for anyone to determine how good or bad the air quality is inside an air-conditioned space due to the lack of accurate, low cost and easy to use instrumentation, the fresh air damper is seldom kept open or utilized at all. Thus, most of the time the conditioned air is simply re-circulated from and into a space. This is particularly the preferred mode of operation for one's air-conditioner when the outdoor air is hot and humid. By letting hot and humid air, even though it is fresh, into the conditioned space, one not only pays more because the air-conditioner has to be run at maximum capacity most of the time, the temperature and humidity of the conditioned air in the space may not be able to be maintained according to one's wishes. Thus, one's comfort, based upon one's preferred air temperature and humidity settings, might also have to be compromised as well.

In short, manufacturers of air-conditioners today simply do not address the Indoor Air Quality (IAQ) issue. They would leave this to the users at large. Thus it is up to one to determine for oneself whether or not to open the fresh air damper in order to attain better indoor air quality but at the expense of more energy or money spent and even possibly compromising one's own comfort. A more realistic look at the currently prevailing air-conditioner dilemma is simply the non-existence of an adequate fresh air controller, preferably built into the air-conditioner unit, that is accurate, reliable, low-cost and easy to use so as to be able to automatically optimize the unit's operating conditions against air quality, comfort and energy savings according to the number of people (zero or otherwise) present in the conditioned space. It is therefore the object of the current invention to advance such a fresh air controller possessing the desirable characteristics and meeting all the functional requirements set forth above.

SUMMARY OF THE INVENTION

The present invention is generally directed to a method of controlling an air conditioner with a cooling unit, a fan and a fresh air damper by obtaining a $CO_2$ concentration measurement from an enclosed space serviced by the air conditioner and then using the $CO_2$ concentration measurement to control when the cooling unit, the fan and the fresh air damper are active or non-active according to a preselected set of rules.

In a first, separate group of aspects of the present invention, a preselected set of rules can cause the cooling unit, the fan and the air damper to be turned off when the $CO_2$ concentration measurement is below a first threshold value, turn the fan on when the $CO_2$ concentration measurement is above a second threshold value, turn the cooling unit on when the $CO_2$ concentration measurement is above a third threshold value, partially open the fresh air damper when the $CO_2$ concentration measurement is above a fourth threshold value but below a fifth threshold value and fully open the fresh air damper when the $CO_2$ concentration measurement is above the fifth threshold value. Alternatively, the cooling unit can be turned off when the $CO_2$ concentration measurement is below a first threshold value and the temperature of air in the enclosed space is below a temperature threshold, or the fan can be turned on even when the $CO_2$ concentration measurement is below the second threshold value when an override condition is selected or when a comfort level trigger is triggered. Also, the preselected set of rules can be subject to a user override, or be varied by a user, or the user can select the preselected set of rules from multiple sets of preselected rules, or the user can override or modify at least one of the preselected set of rules.

In other, separate aspects of the present invention, an air conditioner with a cooling unit, a fan and a fresh air damper, is also fitted (or even retrofitted) with a CO2 concentration measurement device, such as a single-beam NDIR CO2 detector capable of measuring CO2 concentration in parts per million units with a drift over five years of 500 ppm or less, and a controller that uses CO2 concentration measurements to control when the cooling unit, the fan and the fresh air damper are active or non-active according to a preselected set of rules. The air conditioner can be physically mounted in an opening between the enclosed space and an outside space, and can be a window unit or a mini-split unit.

In still other, separate aspects of the present invention, a fresh air controller can directly interface with an electromechanical circuit of an air-conditioner for controlling operating settings of the air-conditioner. The fresh air controller can be made from a short metal tubing of a small diameter with reflective inner walls having at least one small opening on its side, an infrared source secured at one end of the tube, an infrared detector secured at the opposite end of the tube, two small tubings secured and inserted partway into the two respective side openings for allowing gas to traverse the length of the metal tubing, an electronic driver for the infrared source, and an electronic and signal processor to receive signals from the infrared detector, generate a CO2 level and execute an appropriate control function according to the CO2 level so detected. The infrared source can be a tungsten filament vacuum incandescent lamp driven by a quasi-constant power driver circuit to operate the lamp at a reduced recommended power capacity, such as approximately 80%, to increase the lamp's life and reduce its output. The infrared detector can be a single thermopile detector with a narrow bandpass filter and a themistor, wherein the narrow bandpass filter has a specification of a center wavelength substantially equal to 2,332 cm−1, a Full Width at Half maximum substantially equal to 75 cm−1 and a transmittance of greater than 0.70, while the infrared detector can be a pyroelectric type. The two small tubings can be connected to a built-in Venturi-Bernoulli air sampling mechanism or to a Pitot tube arrangement.

Accordingly, it is a primary object of the present invention to provide an improved, electronic controller useful in regulating air conditioners having a fan, a cooling unit and a fresh air damper.

This and further objects and advantages will be apparent to those skilled in the art in connection with the drawings and the detailed description of the preferred embodiment set forth below.

DETAILED DESCRIPTION OF THE PREFERRED EMBODIMENT

The current invention takes advantage of the fact that Carbon Dioxide (CO2) gas concentration measured in Parts-Per-Million (PPM) is a very effective surrogate indicator of human presence in an enclosed space. Outdoor in the countryside where there are few automobiles or heavy machines operating, the CO2 level is typically in the 400-500 PPM range. In an enclosed space in the city, such as inside an apartment or house where nobody is assumed to be present, the CO2 level seldom exceeds 600 PPM. However, when there is just one person inside a closed space of several hundred sq. ft., e.g. with all the windows and door closed or with an air-conditioning unit running but with the fresh air damper fully shut, the CO2 level can quickly rise to more than 1,000 PPM and continue to increase slowly. Under the same enclosed space condition and even with the square footage doubled, two or more persons can, within a relatively short time (e.g. 30 minutes or so), get the CO2 level to exceed 2,000 PPM. If still more people find themselves inside the same enclosed space with no supply of fresh air, the CO2 level can in time reach 4,000 PPM or more. According to the ASHRAE standard 62-1989 and its addendum 62a-1990, adequate indoor ventilation of an enclosed space is tantamount to maintaining a CO2 level of not more 1,000 PPM. Thus, by measuring the CO2 level prevailing in an enclosed space over time, it is possible to estimate the state of the indoor air quality according to ASHRAE standards and also approximately the number of people occupying the said enclosed space.

Therefore, the current invention advances a compact, accurate and reliable CO2 sensor or detector with a host of novel features that make it function as a fresh air controller or multiple-setting switch for air-conditioners. The name of this controller is called the "Capno-Switch" since the Greek word "Capno" means smoke. As is well-known, where there is smoke there is fire, and CO2 usually accompanies fire or combustion. Thus it is common to use the Greek word "Capno" interchangeably with CO2. The Capno-related word of "Capnometer" referring to a highly accurate medical CO2 analyzer used in the ICU's, "Capnogram", the end-tidal CO2 waveform of one's exhaled breath and "Capnograph" the study and analysis of Capnograms—are all in common use today. However, a conventional, high quality, accurate and reliable CO2 sensor will not function well as the kind of fresh air controller in question. It will be far too expensive, too bulky and with performance features and characteristics irrelevant, over-designed or simply not useful to function as such a device. The current invention uses a single-beam, namely one infrared source and one detector, methodology to measure CO2 gas concentration. It is well-known in the art that such a conventional single-beam implementation simply cannot achieve the long-term stability or measurement accuracy for CO2 gas concentrations. Instead, a more expensive dual-beam (one source and two detectors) approach must be deployed to achieve such. In order to make the single-beam methodology work, the current invention enlists the use of a constant power driver, in lieu of the conventional constant voltage or constant current one, to operate an incandescent tungsten lamp as the infrared source. It is well-known in the art that the hot impedance of an incandescent tungsten lamp will steadily increase as the lamp ages, causing the radiant power from the incandescent source to slowly decrease and the sensor output to drift over time, unless the lamp driver is of the constant-power type.

In order to compensate for the spectral shift over time for the center wavelength (CWL) of the narrow bandpass interference filter, the spectral location (CWL) of the current filter is made to coincide precisely with the "Q" branch of the 4.26 microns $CO_2$ absorption band. Furthermore, the Full Width at Half maximum (FWHM) of the filter is designed to cover the entire "P, Q and R" branches or approximately 0.14 microns. These special specifications for the design of the current invention filter minimize to a large extent the aging influence of the filter itself to the output drift of the $CO_2$ sensor.

Finally, in order to render the current fresh air controller compact and low-cost, the Optical Bench Assembly (OBA) is designed out of a relatively short (~2.5 inches) aluminum tube with a very small (~0.250") diameter. The incandescent lamp and infrared detector are installed respectively at each end of the tube. A Venturi-Bernoulli type air sampling mechanism (commonly referred to as the Pitot tube implementation) is further built into the OBA. The end result is an extremely low-cost, rugged, compact and high performance $CO_2$ sensor functioning effectively as a built-in fresh air controller for air-conditioners.

This, in turn, can be used to control an air conditioner according to one or more preselected set of rules.

Figure 1:
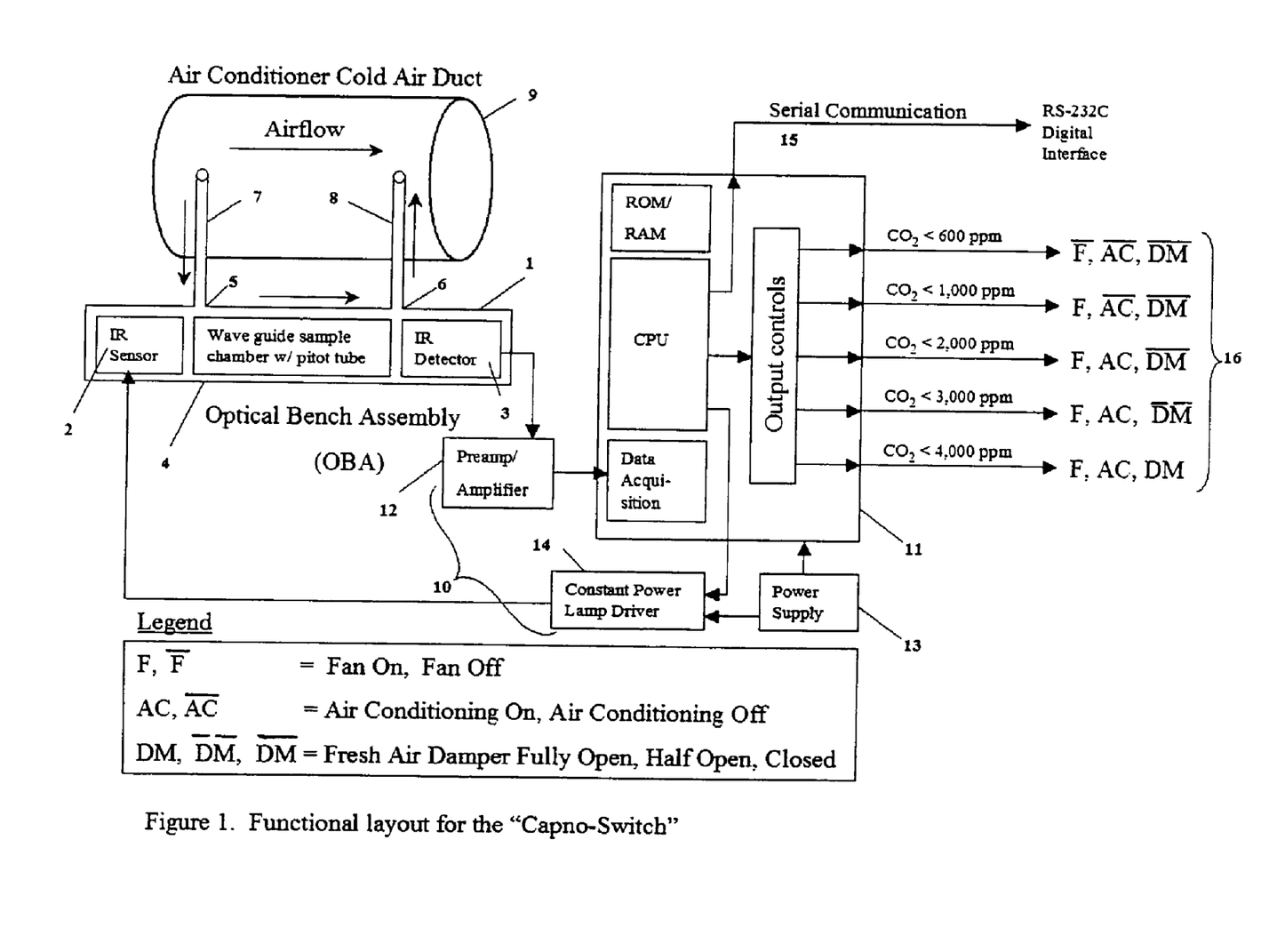
FIG. 1 is a schematic and functional layout drawing for the "Capno-Switch".

The current invention will now be described in even greater detail by reference to a preferred embodiment in which the Capno-Switch is, in essence, a Non-Dispersive Infrared (NDIR) Carbon Dioxide ($CO_2$) sensor incorporating a number of novel features that enable it to function effectively as a fresh air controller for air-conditioners. A schematic and functional layout for the Capno-Switch is shown in FIG. 1. Before describing in detail the novel features relating to $CO_2$ detection that have been incorporated into this device, its functional layout, which comprises two main parts as depicted in FIG. 1, will first be briefly described.

Part I is the Optical Bench Assembly (OBA) 1 with an infrared source 2 mounted at one end and an infrared detector 3 at the other end of the waveguide sample chamber 4 implements a conventional single-beam NDIR $CO_2$ detector. Two lineal small openings 5 and 6 are located on the side of the sample chamber 4. Each is attached with a protruding metal tubing 7 and 8 respectively, forming a built-in Venturi-Bernoulli type air sampling mechanism commonly referred to as the Pitot tube sampling arrangement. The protruding tubes 7 and 8 are to be inserted into the center of the air-conditioner's cold air duct 9 so as to effectively direct a small amount of the flowing air through the sample chamber 4 of the Capno-Switch for $CO_2$ level measurement as depicted in FIG. 1. Alternatively, tubes 7 and 8 can be replaced with a conventional Pitot tube sampling kit (not shown) which effectively connects the openings 5 and 6 of the Capno-Switch to the center of the air duct 9 enabling the Capno-Switch to measure the $CO_2$ level of the air flowing in duct 9. Note that moisture condensation of the air coming in from the cold air duct is not a problem for the sample chamber because 1) the flow rate is very small for Venturi-Bernoulli type air sampling mechanism and 2) the infrared source (see below) generates quite a bit of heat to keep any moisture from condensing.

In an especially preferred embodiment, the waveguide sample chamber 4 is fabricated out of an aluminum tube (e.g. 6061-T6) with reflective inner wall and having a length of ~3.00" and an outside diameter of ~0.25". The infrared source 2 located at one end of the sample chamber 4 is preferably a miniature tungsten filament incandescent lamp operated at ~80% of its recommended power capacity. The infrared detector 3 located at the opposite end of the sample chamber 4 is preferably a thermopile detector die-attached on a size TO-18 header with a narrow bandpass interference filter (to be described in detail below) hermetically sealed on the top of the TO-18 can to form the infrared detector package 3. Tubes 7 and 8 are preferably made out of thin wall 316 grade stainless steel tubing and having an outside and inside diameter of 0.109" and 0.085" respectively.

Part II is a Signal Processor Unit 10 comprising a microprocessor 11, a preamplifier/amplifier circuit 12, power supply block 13 and a constant power IR source or lamp driver 14. The analog signals received by the infrared detector 3 is first conditioned and amplified by preamplifier/amplifier circuit 12 before being routed to the microprocessor 11 for A/D (analog to digital) conversion and for further signal processing and analysis. In addition to providing a serial digital interface 15 to the outside world via the microprocessor's RS232C port, the microprocessor 11 also provides all the output control signals 16 to the electromechanical circuit of the air-conditioner for functioning as a fresh air controller.

The novel features that are incorporated into the Capno-Switch shown in FIG. 1 will now be described in even greater detail. As discussed earlier, without the incorporated novel features, the Capno-Switch can simply be looked upon as a conventional single-beam NDIR $CO_2$ detector. For cost reasons, the use of a high performance conventional dual-beam NDIR $CO_2$ detector is deemed too expensive for the current application in many instances. However, knowing that the single-beam deployment for the NDIR $CO_2$ sensor cannot achieve the type of long-term measurement stability and accuracy required of the Capno-Switch, some special specifications and/or modifications must be implemented into its components in order to overcome this long-term instability or output drift problem.

First and foremost, it is well-known in the NDIR detector art that the operating life and output changes over time for a tungsten filament vacuum type incandescent lamp used as an infrared source is an extremely strong function of the power applied to operate it. For example, a decrease of ~30% of the recommended operating power would increase the life and decrease the output changes for the lamp over time by as much as a factor of ~15. Thus for a lamp having a nominal life of 50,000 hrs or ~5.7 years at 100% of its recommended operating power would extend its life to a staggering 86 years by merely reducing its operating power by ~30%. Notwithstanding, one cannot however arbitrarily reduce the power output of the infrared source for minimizing its output changes over time because the degradation of the system S/N (Signal to Noise ratio) as a result of the reduced source power must also be taken into consideration. Such a S/N degradation is compensated for in the present especially preferred embodiment by the special design of the OBA as shown in FIG. 1. In this case, not only the sizes of the lamp 2 and thermopile detector 3 are specified to fit exactly to the inside diameter of the waveguide sample chamber 4 in order to maximize the power transfer, the reflectivity of the inside wall of the sample chamber must also be rendered as high as possible (>~0.9), so the combined effect on the system S/N enhancement allows one to operate the lamp at approximately 80% reduced power without any S/N degradation.

Figure 2:
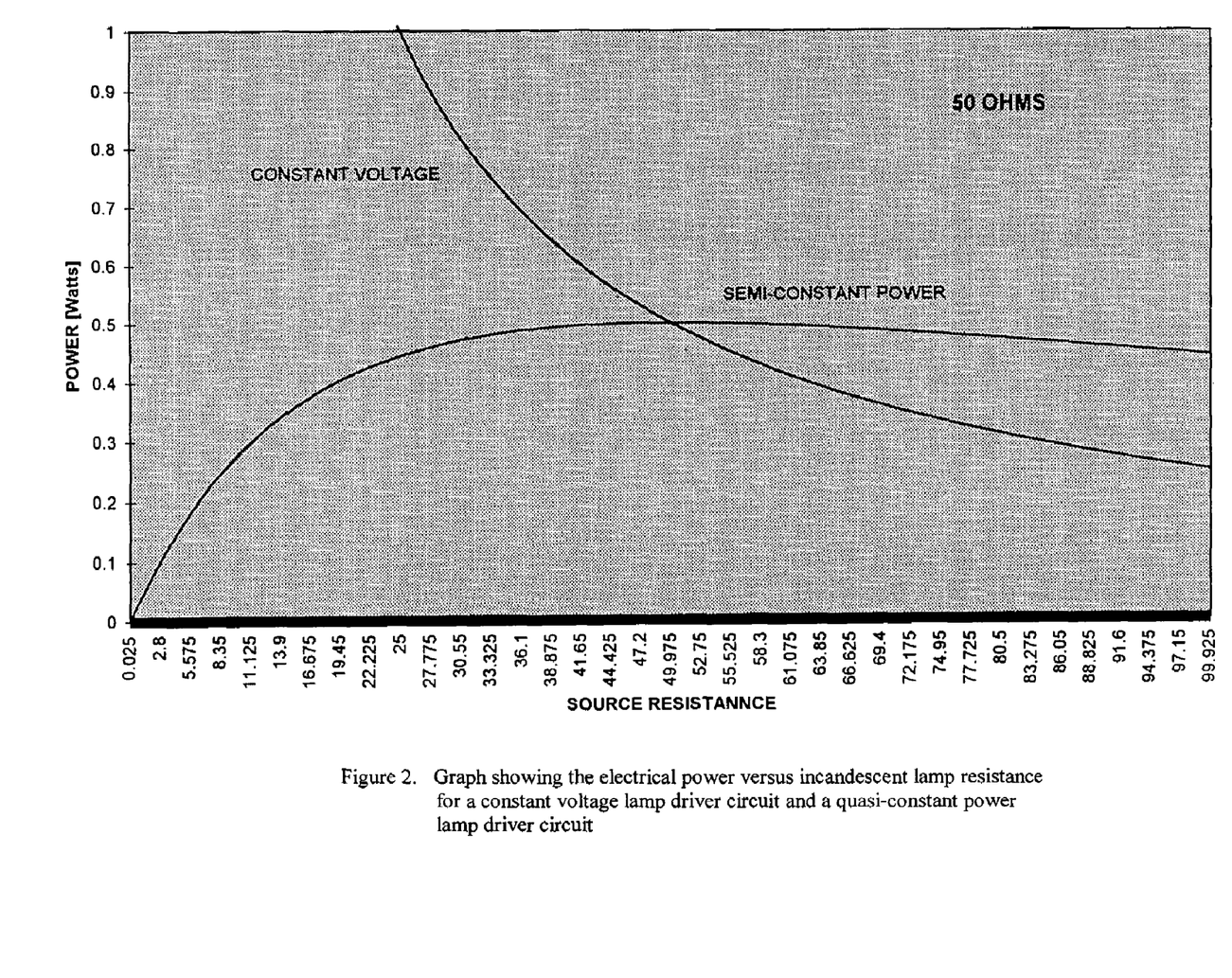
FIG. 2 is a graph showing the electrical power versus incandescent lamp resistance for a constant voltage lamp driver circuit and a semi-constant power lamp driver circuit.
Figure 3:
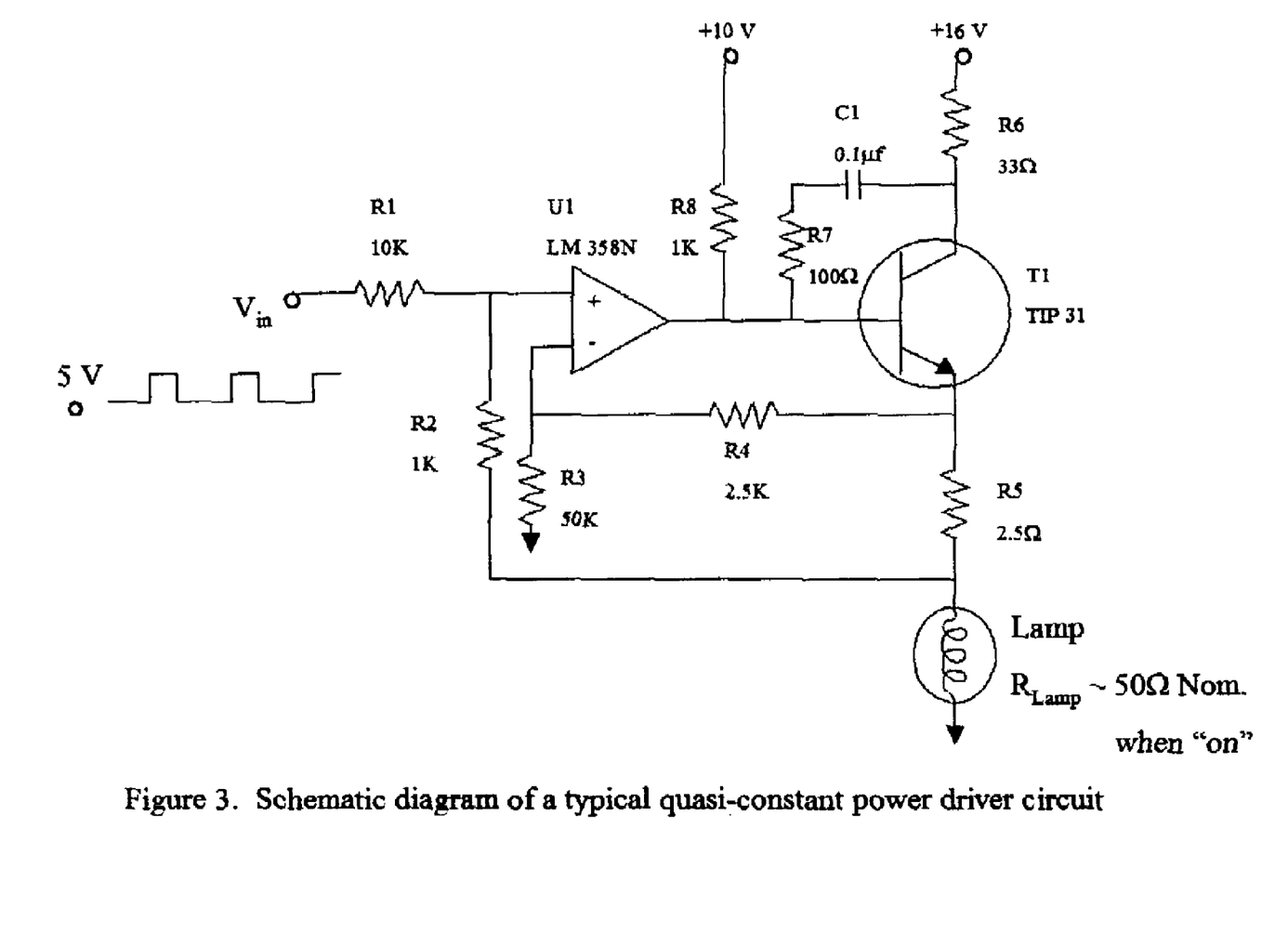
FIG. 3 is a schematic diagram of a typical quasi-constant power driver circuit.

Unfortunately even if one operates the tungsten filament vacuum lamp at 80% reduced power, the output of the lamp would still decrease over time due to the fact that the resistance of the tungsten filament will increase over time. This is readily understandable as the loss of tungsten over time due to evaporation will gradual diminish the filament diameter leading to an increase in resistance. This increase in resistance would lead to a decrease in output power over time if one uses either a constant voltage or constant current driver circuit to operate the lamp. However, if one uses a constant power or semi-constant driver circuit to operate the lamp, the decrease in the lamp output is significantly reduced as shown in FIG. 2. The reason for using a semi-constant power driver circuit rather than an exact constant power one in FIG. 2 is that the latter is very difficult to implement in practice due to the variability of lamp resistances during their production. In FIG. 2 the electrical power driving an incandescent lamp is plotted against the tungsten filament resistance. The cold resistance of the lamp is typically ~5 ohms and the hot resistance at 500 mW output power is typically 50 ohms. One can see from FIG. 2 that as the source resistance increases over time, the lamp output decreases much faster for the constant voltage driver circuit than for the corresponding semi-constant power driver circuit. The schematic circuit of a typical semi-constant power driver for the incandescent lamp is shown in FIG. 3. One can see from the circuit in FIG. 3 that any lamp resistance increase over time would lead to a positive feed back to the voltage that is driving the lamp. Thus, using the semi-constant driver circuit to operate the lamp, the decrease in its output power due to an increase of the source resistance over time will be substantially compensated for by an increase in the driving voltage for the lamp. It is therefore an especially preferred embodiment of the present invention to use a semi-constant power driver circuit to operate the lamp at a 80% reduced power in order to minimize its $CO_2$ measurement output inaccuracies over time.

Figure 4:
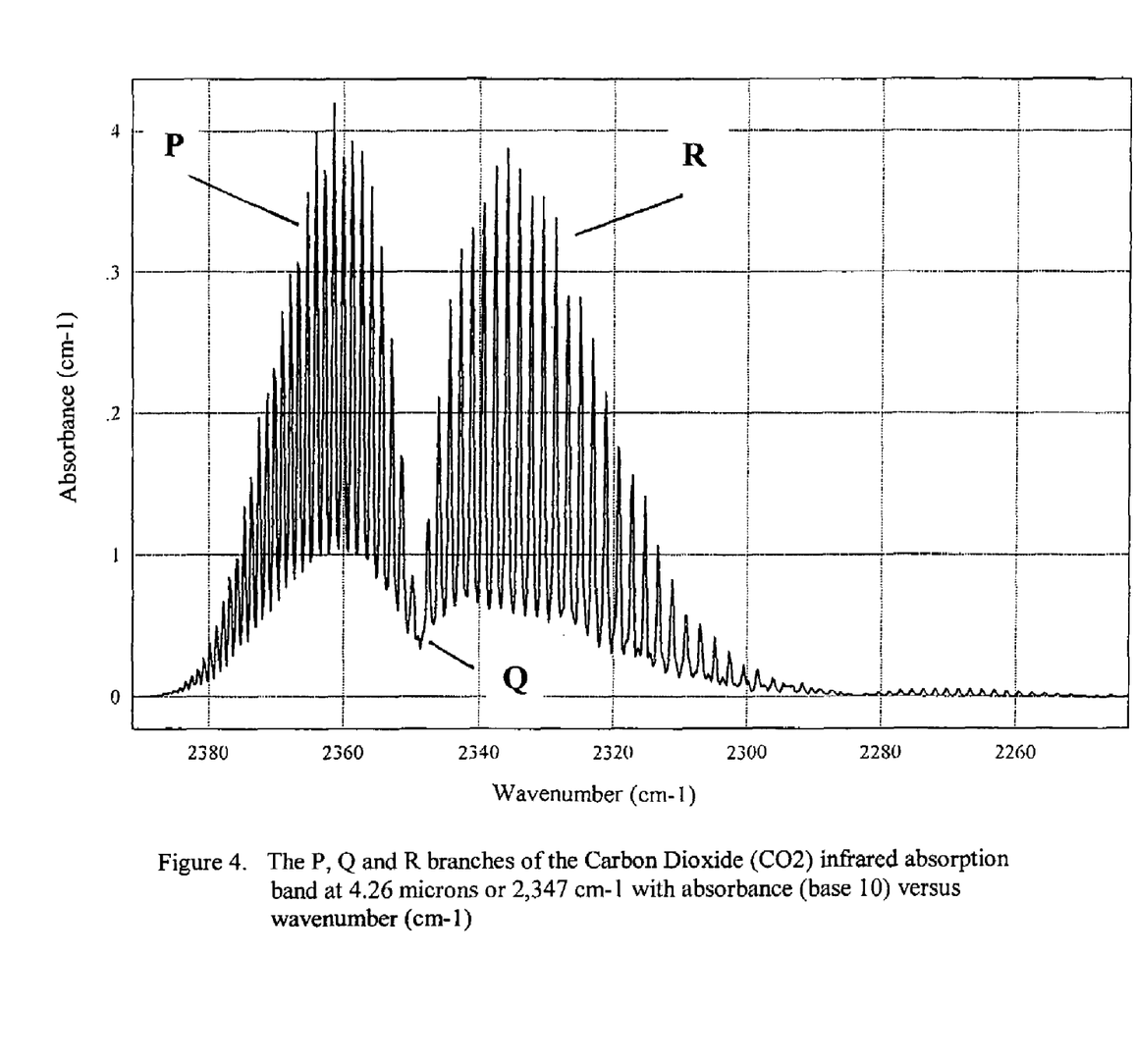
FIG. 4 shows the P, Q and R branches of the Carbon dioxide (CO2) infrared absorption band at 4.26 microns or 2,347 cm−1 with absorbance (base 10) versus wavenumber (cm−1).

Power output variance of the tungsten filament vacuum incandescent lamp over time is not the only ill that the single-beam implementation for the NDIR $CO_2$ detector has to overcome. The shifting of the center wavelength (CWL) and the changes for the FWHM and the CWL transmittance of the narrow bandpass filter that passes only radiation with wavelength lying within the $CO_2$ infrared absorption band also cause significant inaccuracies for $CO_2$ measurements in the course of time. The ill effect caused by the shifting of the CWL is far more important than that attributable to the other variations of the filter characteristics over time. FIG. 4 shows the P, Q and R branches of the relevant $CO_2$ infrared absorption band at 4.26 microns or 2,347 $cm-1$. The extent of the $CO_2$ absorption band spans from 2,295 $cm-1$ to 2,370 $cm-1$ or from 4.22 to 4.36 microns. There are two important specifications for the narrow bandpass filter that the especially preferred embodiment of the present invention must make in order to minimize the $CO_2$ measurement inaccuracies for the Capno-Switch. They are, respectively, the CWL and the FWHM. The CWL must be chosen to lie at the center of the 2,347 $cm-1$ $CO_2$ absorption band as accurately as possible. Thus the CWL should be specified to be at 2,332 $cm-1$ with standard tolerance guaranteed by the filter manufacturer. This is to prevent the CWL of the filter from ever falling outside of the $CO_2$ absorption band thereby producing large $CO_2$ measurement errors when the Capno-Switch is used for a long period of time (>5 years).

The second important specification for the filter is its FWHM. For the same reason that the variation of the characteristics for the filter over time must not cause the wavelength of the selected radiation passed by the filter to ever fall outside of the 4.26 micron $CO_2$ absorption band even as the filter ages, its FWHM must be specified to be equal to the spectral extent of the $CO_2$ absorption band or ~0.14 microns (~75 $cm-1$). This way the filter will always cover spectrally a significant portion of the 4.26 microns $CO_2$ absorption band and the aging effects of the filter on the $CO_2$ measurement inaccuracy would largely be eliminated.

With the novel and simplistic implementation of the Optical Bench Assembly (OBA) described earlier with FIG. 1 and the specifications for the infrared source (tungsten filament vacuum incandescent lamp) in its operation and the infrared detector (thermopile detector) in its integral narrow bandpass interference filter, a simple single-beam NDIR $CO_2$ detector can be transformed into a rugged, stable and extremely low-cost Capno-Switch or a fresh air controller for air-conditioners. Even with the novel features incorporated into and stringent specifications imposed on the components of the Capno-Switch, there will still be a certain amount of $CO_2$ measurement inaccuracies over long period of time. However, because the Capno-Switch is not being used quantitatively as a $CO_2$ analyzer where one has to know precisely the $CO_2$ level in PPM to very high accuracy, the fact that it is only be used as a multi-setting $CO_2$ switch makes this small measurement error over time tolerable and relatively unimportant. The reason for drawing this conclusion can be explained further as follows.

Referring back to FIG. 1, the object of the present Capno-Switch is to function as a fresh air controller for an air-conditioner and as such it controls the fan F, the cooling unit AC and the fresh air damper DM, which allows the influx of fresh air from the outside when it is open or half-open, of the air-conditioner. One especially preferred embodiment is to have five control settings for a particular air-conditioner corresponding to the $CO_2$ level measured in the cold air duct as <600 PPM, <1,000 PPM, <2,000 PPM, <3,000 PPM and <4,000 PPM, respectively. Even with a nominal $CO_2$ setting hysteresis of 10%, the safe range for the Capno-Switch to drift over time before it will affect the multiple-settings for the control of the $CO_2$ level in the cold air duct is hundreds of PPM. Thus, with the novel features of the present invention incorporated into the conventional single-beam $CO_2$ detector, the relatively small $CO_2$ measurement error to be expected of the Capno-Switch over time is deemed operationally tolerable and relatively insignificant.

An example of an especially preferred embodiment for the Capno-Switch to control the fan F, Cooling Unit AC and the fresh air damper DM is presented as follows. When the measured $CO_2$ level in the cold air duct is <600 PPM indicative of the fact that there is nobody in the conditioned space in question, the Capno-Switch will turn off all the relevant functions of the air-conditioner, namely the fan F, the Cooling Unit AC and the fresh air damper DM will all be shut off. When the measured $CO_2$ level is <1,000 PPM, only the fan F is turned on. When the measured $CO_2$ level is <2,000 PPM, both the fan F and the Cooling Unit AC will be turned on but the fresh air damper DM remains shut. When the measured $CO_2$ level is <3,000 PPM, both the fan F and the Cooling Unit AC will remain "ON" while at the same time the fresh air damper DM will be opened half-way. Finally, if the measured $CO_2$ level is above 3,000 PPM, not only do the fan F and the Cooling Unit AC remain "ON", the fresh air damper DM will now be fully open so as to bring in as much fresh air as possible from the outside to the conditioned space. Thus, it is clear that the present invention, viz. the Capno-Switch, is capable of addressing automatically the air quality issue within a conditioned space using $CO_2$ level as the surrogate human presence indicator. Furthermore, it has the potential to save energy as it will effectively shut down the entire air-conditioner unit when it detects that nobody is in the conditioned space (CO2 level <600 PPM).

The present invention also lends itself to customization by different manufacturers, for different intended uses, or for customization by the end users. Once one understands the teaching of the present invention that a CO2 concentration measurement can be used to control when the cooling unit, the fan and the fresh air damper are active or non-active according to a preselected set of rules, many different sets of rules can be developed or adopted to fit different scenarios, and the rules can be subject to modification or exceptions or even to an override condition. For example, even though a preselected set of rules might cause the cooling unit, the fan and the air damper to be turned off when the CO2 concentration measurement is below a first threshold value, the rules can be modified to leave the cooling unit and/or the fan on if the temperature of air in the enclosed space is below a temperature threshold or when an override condition is selected or when a comfort level trigger is triggered. Or, to give another example, certain rules might be modified, overrode or varied based upon external conditions, such as time of day, to minimize use of power during peak periods when energy is most expensive. In addition, a user can be allowed to select the preselected set of rules that will be applied in a given unit from a plurality of preselected rules, or override at least one of the preselected set of rules, or even modify at least one of the preselected set of rules.

Moreover, the customization achievable by the present invention can be incorporated into relatively inexpensive, personal air conditioners. For example, a fresh air controller incorporating the teachings of this invention can be incorporated into a window-mounted air conditioner, or into a "mini-split" unit. Mini-split units were originally developed in Japan and consist of an indoor wall-mounted fan/evaporator unit and an outdoor compressor/condenser combination. The two units are connected via tubes through which liquid and vapor refrigerant flow. Both window units and mini-split units are ideally suited for small living areas, in the range of 300 square feet or so, and even for larger areas of 500-600 square feet, and such spaces are especially well-suited to application of the teachings of the present invention.

While the invention has been described herein with reference to certain preferred embodiments, those embodiments have been presented by way of example only, and not to limit the scope of the invention. Additional embodiments thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. An air conditioner with a cooling unit, a fan and a fresh air damper, further comprising:
   a CO2 concentration measurement device for obtaining a CO2 concentration measurement from an enclosed space serviced by the air conditioner; and
   a controller that uses measurements from the CO2 concentration measurement device to control when the cooling unit, the fan and the fresh air damper are active or non-active according to a preselected set of rules;
   wherein the CO2 concentration measurement device is comprised of a single-beam NDIR CO2 detector capable of measuring CO2 concentration in parts per million units with a drift over five years of 500 ppm or less.

2. The air conditioner of claim 1, wherein the air conditioner is a window unit.

3. The air conditioner of claim 1, wherein the air conditioner is a mini-split unit.

4. The air conditioner of claim 1, wherein the preselected set of rules will cause the cooling unit, the fan and the air damper to be turned off when the CO2 concentration measurement is below a first threshold value.

5. The air conditioner as recited in claim 4, wherein the preselected set of rules will turn the cooling unit off when the CO2 concentration measurement is below a first threshold value and the temperature of air in the enclosed space is below a temperature threshold.

6. The air conditioner as recited in claim 1, wherein the preselected set of rules will turn the fan on when the CO2 concentration measurement is above the second threshold value.

7. The air conditioner as recited in claim 4, wherein the preselected set of rules will turn the fan on when the CO2 concentration measurement is above the second threshold value.

8. The air conditioner as recited in claim 7, wherein the fan can be turned on even when the CO2 concentration measurement is below the second threshold value when an override condition is selected.

9. The air conditioner as recited in claim 4, wherein the preselected set of rules will turn the fan on when the CO2 concentration measurement is above the second threshold value or when a comfort level trigger is triggered.

10. The air conditioner as recited in claim 1 wherein the preselected set of rules will turn the cooling unit on when the CO2 concentration measurement is above a third threshold value.

11. The air conditioner as recited in claim 7, wherein the preselected set of rules will turn the cooling unit on when the CO2 concentration measurement is above a third threshold value.

12. The air conditioner as recited in claim 1, wherein the preselected set of rules will partially open the fresh air damper when the CO2 concentration measurement is above a fourth threshold value but below a fifth threshold value.

13. The air conditioner as recited in claim 11, wherein the preselected set of rules will partially open the fresh air damper when the CO2 concentration measurement is above a fourth threshold value but below a fifth threshold value.

14. The air conditioner as recited in claim 1, wherein the preselected set of rules will fully open the fresh air damper when the CO2 concentration measurement is above the fifth threshold value.

15. The air conditioner as recited in claim 13, wherein the preselected set of rules will fully open the fresh air damper when the CO2 concentration measurement is above the fifth threshold value.

16. The air conditioner as recited in claim 1, wherein the preselected set of rules is subject to a user override.

17. The air conditioner as recited in claim 1, wherein the preselected set of rules can be varied by a user.

18. The air conditioner as recited in claim 1, wherein the preselected set of rules can be modified by a user.

19. The air conditioner as recited in claim 1, wherein the air conditioner is physically mounted in an opening between the enclosed space and an outside space.

20. A fresh air controller that directly interfaces with an electromechanical circuit of an air-conditioner for controlling operating settings of the air-conditioner, the air conditioner having a fan, a cooling unit and a fresh air damper, comprising:
- a short metal tubing of a small diameter with reflective inner walls having two small openings on its side;
- an infrared source secured at one end of the tube;
- an infrared detector secured at the opposite end of the tube;
- two small tubings secured and inserted partway into the two respective side openings for allowing gas to traverse the length of the metal tubing;
- an electronic driver for the infrared source; and
- an electronic and signal processor to receive signals from the infrared detector, generate a $CO_2$ level and execute an appropriate control function according to the $CO_2$ level so detected.

21. The fresh air controller of claim 20, wherein the infrared source is comprised of a tungsten filament vacuum incandescent lamp.

22. The fresh air controller of claim 21, wherein the electronic driver for the lamp is comprised of a quasi-constant power driver circuit for operating the lamp at a reduced recommended power capacity to increase the lamp's life and reduce its output.

23. The fresh air controller of claim 22, wherein the reduced recommended power capacity is approximately 80%.

24. The fresh air controller of claim 22, wherein the infrared detector is comprised of a single thermopile detector with a narrow bandpass filter and a themistor.

25. The fresh air controller of claim 24, wherein the infrared detector is a pyroelectric type.

26. The fresh air controller of claim 25, wherein the narrow bandpass filter has a specification of a center wavelength substantially equal to 2,332 cm−1, a Full Width at Half maximum substantially equal to 75 cm−1 and a transmittance of greater than 0.70.

27. The fresh air controller of claim 20, wherein the two small tubings are connected to a built-in Venturi-Bernoulli air sampling mechanism.

28. The fresh air controller of claim 20, wherein the two small tubings are connected to a built-in Pitot tube arrangement.

29. An air conditioner with a cooling unit, a fan and a fresh air damper, further comprising:
- a $CO_2$ concentration measurement device for obtaining a $CO_2$ concentration measurement from an enclosed space serviced by the air conditioner; and
- a controller that uses measurements from the $CO_2$ concentration measurement device to control when the cooling unit, the fan and the fresh air damper are active or non-active according to a preselected set of rules;
- a short metal tubing of a small diameter with reflective inner walls having two small openings on its side;
- an infrared source secured at one end of the tube;
- an infrared detector secured at the opposite end of the tube;
- two small tubings secured and inserted partway into the two respective side openings for allowing gas to traverse the length of the metal tubing;
- an electronic driver for the infrared source; and
- an electronic and signal processor to receive signals from the infrared detector, generate a $CO_2$ level and execute an appropriate control function for the controller according to the $CO_2$ level so detected.

* * * * *